(12) United States Patent
Sills

(10) Patent No.: US 7,482,305 B1
(45) Date of Patent: Jan. 27, 2009

(54) HERBICIDE COMPOSITION AND METHOD FOR DRY AND DRILL SEEDED RICE

(76) Inventor: David P. Sills, 3301 Stonehurst Dr., El Dorado Hills, CA (US) 95762

( * ) Notice: Subject to any disclaimer, the term of this patent is extended or adjusted under 35 U.S.C. 154(b) by 0 days.

(21) Appl. No.: 11/544,369

(22) Filed: Oct. 6, 2006

Related U.S. Application Data

(60) Provisional application No. 60/724,072, filed on Oct. 6, 2005.

(51) Int. Cl.
*A01N 25/00* (2006.01)
*A01N 65/00* (2006.01)

(52) U.S. Cl. .................. 504/116.1; 504/189

(58) Field of Classification Search ............. 504/116.1, 504/189
See application file for complete search history.

(56) References Cited

U.S. PATENT DOCUMENTS 5,552,367 A * 9/1996 Gamblin et al. ............. 504/138
5,567,670 A * 10/1996 Amuti et al. ................. 504/230
5,679,619 A * 10/1997 Morgan et al. .............. 504/130
5,741,502 A * 4/1998 Roberts ...................... 424/405

* cited by examiner

*Primary Examiner*—Sreeni Padmanabhan
*Assistant Examiner*—Mei-Ping Chui
(74) *Attorney, Agent, or Firm*—Audrey A. Millemann; Weintraub Genshlea et al.

(57) ABSTRACT

The invention is a liquid composition, and method of use, for a pre-rice-seed-germination herbicide for dry or drill seeded rice. The composition includes pendimethalin and pinolene. It is applied in a spray volume of about 18.9-75.7 L per ha (5-20 gal per acre) of rice. After applying the herbicide, the field is flush irrigated with water. The composition is not phytotoxic and significantly reduces the amount of weed germination.

3 Claims, No Drawings

HERBICIDE COMPOSITION AND METHOD FOR DRY AND DRILL SEEDED RICE

CROSS-REFERENCE TO RELATED APPLICATION

The present application claims the benefit of U.S. provisional patent application number 60/724,072 filed on Oct. 6, 2005 and entitled "Pendimethalin/Pinolene Product for Dry Seeded Rice," which is hereby incorporated by reference.

BACKGROUND OF THE INVENTION

1. Field of the Invention

The invention relates generally to crop herbicides, and, in particular, to an herbicide that contains pendimethalin and pinolene for dry and drill seeded rice.

2. Description of the Related Art

Pendimethalin has been used as a rice herbicide for dry and drill seeded rice throughout the world for many years. The use of pendimethalin, however, has been strictly limited to use after the rice seed has germinated (i.e., after the first irrigation or rainfall). In fact, current and past pendimethalin registrations have expressly prohibited the use of pendimethalin before rice germination. The reason for this limitation is that pendimethalin is a root inhibitor and is therefore toxic to germinating rice seed. As long as pendimethalin is used after the rice seed has germinated, it is not toxic to the rice because it is not in contact with the seed.

The disadvantage of pendimethalin is that it must be used after the rice seed has germinated, which is also after a significant amount of weeds have germinated and begun to grow.

Thus, there is a need for a pre-flush, pre-rice-seed-germination herbicide.

SUMMARY OF THE INVENTION

The invention is a liquid composition that is a pre-flush, pre-rice-seed-germination herbicide for use on dry or drill seeded rice, and a method of use. The composition includes pendimethalin and pinolene.

The composition of the invention is superior to existing pendimethalin in that it can be used as a pre-rice-seed-germination herbicide, which provides rice growers with weed control well before rice seed germination. The earlier weed control is a significant advantage in that it minimizes the number of weeds and increases the crop yield.

The composition also has the benefits of reducing water usage, reducing the need for aerial applications, and minimizing the ground transport of herbicides.

Using the method of the invention, the composition is sprayed before germination of the rice seed and is followed by the addition of moisture.

DETAILED DESCRIPTION OF THE PREFERRED EMBODIMENTS

The composition of the invention includes pendimethalin (N-(1-ethylpropyl)-3,4-dimethyl-2,6-dinitrobenzenamine) and pinolene (also referred to as pinene).

Solvent-based pendimethalin is a bright yellow liquid. Pendimethalin is manufactured by several companies and may be sold as either a solvent-based liquid or a water-based liquid. PROWL® 3.3 (BASF Corporation, Research Triangle Park, N.C.) is a solvent-based pendimethalin that works well in the composition of the invention. PROWL® 3.3 contains 37.4% active ingredient pendimethalin or 1.49 kg (3.3 lbs) active ingredient pendimethalin per 3.78 L (1 gallon). PROWL® H2O is a dark orange liquid, is water based or encapsulated, and contains 38.7% active ingredient pendimethalin or 1.72 kg (3.8 lbs) active ingredient pendimethalin per 3.78 L (1 gallon).

Pinolene is a sticky, amber liquid. It is manufactured under several trade names, including SUSTAIN® and NUFILM P® (Miller Chemical and Fertilizer Company, Hanford, Pa.). SUSTAIN®, which works well in the composition of this invention, is pinene (terpene) polymers, petroleum, a-(p-Dodecylpheny)-Omega-hydroxypoly (oxyethylene).

To prepare the composition of the invention, preferably a solvent-based liquid pendimethalin and a liquid pinolene are mixed together in a chemical-resistant container. Although a solvent-based pendimethalin is preferable, alternatively, a water-based pendimethalin may be used. The ratio of the amount of pendimethalin to the amount of pinolene by volume is preferably about 1.5 to about 1. For example, a preferable composition is made by mixing about 1.13 L (2.4 pints) of pendimethalin and about 0.75 L (1.6 pints) of pinolene, for a total of about 1.89 L (4.0 pints) of liquid composition, which results in a composition that contains about 24-25% active ingredient of pendimethalin by volume and about 12-13% pinolene by volume, with the balance being inert ingredients. This is equivalent to 898 g (1.98 lbs) of active ingredient pendimethalin per 3.78 L (1 gallon).

After combing the two chemicals together, they are thoroughly mixed or agitated.

The composition can be stored at a temperature above about 1.1° C. (34° F.) and below about 37.7° C. (100° F.) for over six months or longer. Preferably, the composition should be agitated before used. Alternatively, the composition may be mixed immediately before used, depending on the needs of the grower.

To use the herbicide composition, 1.89 L (0.5 gallon) of the composition is added to enough water to make a total spray volume of about 18.9 L to about 75.7 L per ha (about 5 gallons to about 20 gallons per acre) of rice seed. The rice seed should preferably be planted by broadcasting or drill seeding about 1.27 cm (0.5 inch) below the surface of the soil, but no deeper than about 2.54-5.08 cm (1-2 inches). The herbicide composition is applied to the field immediately after planting or up to about one week after planting, but before rice seed germination. It is applied by spraying, either from the ground or the air. Moisture is then provided, by rainfall or by fluid irrigation with water, within about ten days after apply the herbicide.

It is believed that the composition is not phytotoxic because the pinolene acts as an adhesive and holds the pendimethalin in the top 6.35-8.33 mm (0.25-0.33 inch) of soil, such that it does not come into contact with the deeper rice seed.

EXAMPLE

The composition of the invention, containing pendimethalin and pinolene, was prepared using PROWL® 3.3 (BASF Corporation) and SUSTAIN® (Miller Chemical and Fertilizer Co.). An 8.09 ha (20 acre) field was planted with two types of rice: 4.04 ha (10 acres) with M-202 and 4.04 ha (10 acres) with Cal-Mochi. The seed rate per 0.4 ha (1 acre) was 30.8 kg (170 lbs) for M-202 and 29 kg (160 pounds) for Cal-Mochi. Seeding was performed by dry seeded broadcast. Incorporation was performed immediately after, using a rice roller. The composition was sprayed by ground on 12 plots of about 0.6 ha (1.5 acres) each, using a total of 75.7 L of spray volume per ha (20 gallons per acre). Each plot was treated with a different treatment (rate or dosage) of the composition. The following treatments were used:
1. Pendimethalin @373 g (2.06 lbs) Active and Pinolene@0.189 L per ha (1 pint per acre).
2. Pendimethalin@299 g (1.65 lbs) Active and Pinolene@0.189 L per ha (1 pint per acre).
3. Pendimethalin@223 g (1.23 lbs) Active and Pinolene@1.89 L per ha (1 pint per acre).
4. Pendimethalin@179.6 g (0.99 lbs) Active and Pinolene@0.302 L per ha (1.6 pints per acre).*
5. Pendimethalin@74.8 g (0.4125 lbs) Active and Pinolene@0.189 L per ha (1 pint per acre).
6. Pendimethalin@373 g (2.06 lbs) Active and Pinolene@0.378 L per ha (2 pints per acre).
7. Pendimethalin@299 g (1.65 lbs) Active and Pinolene@0.378 L per ha (2 pints per acre).
8. Pendimethalin@223 g (1.23 lbs) Active and Pinolene@0.378 L per ha (2 pints per acre).
9. Pendimethalin@179.6 g (0.99 lbs) Active and Pinolene@0.302 L per ha (1.6 pints per acre).*
10. Pendimethalin@74.8 g (0.4125 lbs) Active and Pinolene@0.378 L per ha (2 pints per acre).
11. Pendimethalin@179.6 g (0.99 lbs) Active. No Pinolene.
12. Pendimethalin@373 g (2.06 lbs) Lbs Active. No Pinolene.

*Treatment rate of 179.6 g (0.99 lbs) Active of pendimethalin is the highest rate allowed by current labels and is the reason for that specific treatment level.

Table 1 shows the results of the treatments in % phytotoxicity and % efficacy.

TABLE 1

| | Results | | | | |
|---|---|---|---|---|---|
| | Grams (Pounds) | | Efficacy % | | |
| Treatment | Active Pendimethalin | Phyto-toxicity % | Water-grass | Sprangle-top | Small-flower |
| 1 | 373 (2.06) | 40 | 80 | 90 | 100 |
| 2 | 299 (1.65) | 10 | 100 | 100 | 100 |
| 3 | 223 (1.23) | 0 | 100 | 100 | 100 |
| 4 | 179.6 (0.99) | 0 | 100 | 100 | 100 |
| 5 | 74.8 (0.4125) | 0 | 85 | 95 | 90 |
| 6 | 373 (2.06) | 0 | 100 | 100 | 100 |
| 7 | 299 (1.65) | 0 | 100 | 100 | 100 |
| 8 | 223 (1.23) | 0 | 100 | 95 | 100 |
| 9 | 179.6 (0.99) | 0 | 100 | 100 | 100 |
| 10 | 74.8 (0.4125) | 0 | 85 | 100 | 100 |
| 11 | 179.6 (0.99) | 35 | 80 | 95 | 90 |
| 12 | 373 (2.06) | 50 | 90 | 85 | 90 |

The data shows that there is a range of pendimethalin-pinolene rates that can be used in order to achieve weed control in rice without phytotoxicity or rice seedling damage.

The 373 g (2.06 lb) rate of pendimethalin active demonstrated that the high level of pendimethalin needed a high rate of pinolene to hold the pendimethalin to the soil surface. See Treatment no. 1. Treatment no. 6 has the same high rate of pendimethalin, but contains a higher rate of pinolene (0.378 L (2 pints) and exhibited no phytotoxicity. Therefore, the use of pinolene is demonstrated to hold the pendimethalin to the surface of the soil, thereby eliminating seed exposure to otherwise toxic levels of pendimethalin. Conversely, in treatment nos. 11 and 12, where no pinolene was used, there was significant phytotoxicity.

Weed control efficacy is also demonstrated on susceptible species. Watergrass, Sprangletop and Smallflower were the most common weeds at the site. The use of the composition, at rates that are within the range of historic pendimethalin use in rice, achieved excellent results.

The invention has bee described above with reference to the preferred embodiment. Those skilled in the art may envision other embodiments and variations of the invention that fall within the scope of the claims.

I claim:

1. A method of treating dry or drill seeded rice, for weed control, comprising:
    a) planting dry or drill seeded rice;
    b) before germination of the rice seed, spraying a liquid composition of pendimethalin active and pinolene on the soil; wherein the weight to volume ratio of pendimethalin active to pinolene is between 0.21 lbs; 1 pint and 1.23 lbs; 1 pint;
    c) providing moisture to the rice seed within about 10 days of said spraying.

2. The method of claim 1 further comprising:
    a) wherein said composition contains pendimethalin active in an amount of about 1.98 lbs per gallon, and about 0.5 gallon of said composition is added to enough water to make a total spray volume of about 5 to about 20 gallons; and
    b) wherein said spray is applied in an amount between about 5 to about 20 gallons per acre of planted dry or drill seeded rice.

3. The method of claim 1, wherein said moisture is water provided by flush irrigation or rainfall.

* * * * *